(12) United States Patent
Noguchi et al.

(10) Patent No.: US 7,955,825 B2
(45) Date of Patent: Jun. 7, 2011

(54) PROCESS FOR PRODUCING CMP-N-ACETYLNEURAMINIC ACID

(75) Inventors: Toshitada Noguchi, Choshi (JP); Tomoki Hamamoto, Choshi (JP)

(73) Assignee: Yamasa Corporation, Chiba (JP)

(*) Notice: Subject to any disclaimer, the term of this patent is extended or adjusted under 35 U.S.C. 154(b) by 959 days.

(21) Appl. No.: 10/521,576

(22) PCT Filed: Jan. 15, 2003

(86) PCT No.: PCT/JP03/00258
§ 371 (c)(1),
(2), (4) Date: Jun. 29, 2005

(87) PCT Pub. No.: WO2004/009830
PCT Pub. Date: Jan. 29, 2004

(65) Prior Publication Data
US 2005/0260718 A1    Nov. 24, 2005

(30) Foreign Application Priority Data
Jul. 18, 2002    (JP) .................................. 2002-208987

(51) Int. Cl.
*C12P 7/40* (2006.01)
(52) U.S. Cl. ............... 435/136; 435/41; 435/42; 435/84; 435/132; 435/170; 435/172; 536/1.11; 536/26.8
(58) Field of Classification Search .................. None
See application file for complete search history.

(56) References Cited

U.S. PATENT DOCUMENTS

| | | | |
|---|---|---|---|
| 5,071,750 | A | 12/1991 | Kragl et al. |
| 5,334,514 | A | 8/1994 | Kittelmann et al. |
| 5,811,539 | A | 9/1998 | Seiffert-Stoeriko et al. |
| 5,876,980 | A | 3/1999 | DeFrees et al. |
| 6,332,026 | B1 | 12/2001 | Kuusama et al. |
| 2002/0064836 | A1* | 5/2002 | Koizumi et al. ............ 435/89 |

FOREIGN PATENT DOCUMENTS

| | | |
|---|---|---|
| EP | 0 428 947 A1 | 11/1990 |
| EP | 428947 | 5/1991 |
| EP | 0 524 143 A1 | 1/1993 |
| EP | 0 704 536 A1 | 3/1996 |
| EP | 0 708 177 A1 | 4/1996 |
| EP | 0 578 825 B1 | 3/1997 |
| EP | 1 081 230 A2 | 3/2001 |
| JP | 61-180719 A | 8/1986 |
| JP | 02-177891 | 7/1990 |
| JP | 3-180190 | 6/1991 |
| JP | 5-211884 | 8/1993 |
| JP | 10-4961 | 1/1998 |
| JP | 2001-136982 | 5/2001 |
| JP | 2003-093091 | 4/2003 |
| WO | 95/26399 | 10/1995 |
| WO | 96/32492 A1 | 10/1996 |
| WO | 98/06239 A1 | 2/1998 |

OTHER PUBLICATIONS

Plumbridge & Vimr, Journal of Bacteriology, 1999, vol. 181, No. 1. p. 47-54.*
Tabata et al., Enzyme & Microbial Technology, Mar. 2002, vol. 30, p. 237-333.*
IUBMB enzyme Nomenclature (EC 5.9.3.1).*
Kohno et al., Agric. Biol. Chem., 1983, vol. 47, No. 1, p. 19-24.*
Rodriguez-Aparicio et al., Biochimica et Biophysica Acta, 1999, vol. 1428, p. 305-313.*
IUBMB enzyme nomenclature for EC 4.1.3.3.*
K. Ishige et al. "Novel Method for Enzymatic Synthesis of CMP-NeuAc.", Biosci. Biotechnol. Biochem., Aug. 2001, vol. 65, No. 8, pp. 1736-1740.
M. Kittelmann et al., "CMP-N-Acetyl Neuraminic-Acid Synthetase from *Escherichia coli*: Fermentative Production and application for the preparative Synthesis of CMP-neuraminic Acid", Appl. Microbiol. Biotechnol., Dec. 1995, vol. 44, pp. 59-67.
International Search Report dated Mar. 11, 2003 (PCT/JP03/00258) in the International (PCT) Application of which the present application is the U.S. National Stage.
International Search Report dated Dec. 28, 2004 issued in PCT/JP2004/013760 corresponding to U.S. Appl. No. 10/573,385 having overlapping inventors.
T. Hamamoto et al., "Enzymatic Synthesis of Cytidine 5'-Monophospho-N-acetylneuraminic Acid", Biosci. Biotechnol. Biochem., vol. 69 (10), pp. 1944-1950 (2005).
M. Kittelmann et al., "CMP-N-acetyl neuraminic-acid synthetase from *Escherichia coli*: fermentative production and application for the preparative synthesis of CMP-neuraminic acid", Appl. Microbiol. Biotechnol., vol. 44, pp. 59-67 (1995).
T. Endo et al., "Large-scale production of CMP-NeuAc and sialylated oligosaccharides through bacterial coupling", Appl. Microbiol. Biotechnol., vol. 53, pp. 257-261 (2000). M. Kim et al., "Enzymes in Carbohydrate Synthesis: N-Acetylneuraminic Acid Aldolase Catalyzed Reactions and Preparation of N-Acetyl-2-deoxy-D-neuraminic Acid Derivatives", J. Am. Chem. Soc., 1988, vol. 110, pp. 6481-6486.
E. Simon et al., "Synthesis of CMP-NeuAc from N-Acetylglucosamine: Generation of CTP from CMP Using Adenylate Kinsase", J. Am. Chem. Soc., 1988, vol. 110, pp. 7159-7163.
S. Blayer et al., "Alkaline Biocatalysis for the Direct Synthesis of N-Acethyl-D-Neuraminic Acid (Neu5Ac) from N-Acetyl-D-Glucosamine (GlcNAc)," Biotechnology and Bioengineering, vol. 66, No. 2 (1999).
M. Mahmoudian et al., "An efficient process for production of N-acetylneuraminic acid using N-acetylneuraminic acid aldolase", Enzyme and Microbial Technology, vol. 20, pp. 393-400 (1997).

(Continued)

*Primary Examiner* — Kade Ariani
(74) *Attorney, Agent, or Firm* — Wemderoth, Lind & Ponack, L.L.P.

(57) ABSTRACT

The present invention is directed to a process for producing CMP-N-acetylneuraminic acid (CMP-NeuAc), comprising adding to the cultured *E. coli* cells which has been transformed with both the DNA encoding N-acetylglucosamine-6-phosphate 2-epimerase (GlcNAc-6P 2-epimerase) and the DNA encoding N-acetylneuraminic acid synthase (NeuAc synthase) and exhibit activities of N-acetylglucosamine-6-phosphate 2-epimerase and N-acetylneuraminic acid synthase, a phosphate buffer containing baker's yeast cells, CMP, N-acetylglucosamine (GlcNAc), magnesium, xylene, glucose, and CMP-N-acetylneuraminic acid synthase (CMP-NeuAc synthase) to provide a reaction mixture, and allowing the reaction to proceed and produce CMP-N-acetylneuraminic acid (CMP-NeuAc), and wherein the process does not require adding ATP.

1 Claim, No Drawings

OTHER PUBLICATIONS

S.L. Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives", Glycobiology (1991), vol. 1, No. 2, pp. 187 to 191.

P.J. O'Brien et al., "Functional interrelationships in the alkaline phosphatase superfamily: phosphodiesterase activity of *Escherichia coli* alkaline phosphatase", Biochemistry. (2001) vol. 40, No. 19, pp. 5691 to 5699.

M.A. Nesmeyanova et al., "Multiple forms of alkaline phosphatase from *Escherichia coli* cells with repressed and derepressed biosynthesis of the enzyme", J. Bacteriol (1981) vol. 146, No. 2, pp. 453 to 459.

B. Magnouloux-Blanc et al., "Overproduction and excretion of β-lactamase and alkaline phosphatase by *Escherichia coli* olp mutants", Appl. Microbiol. Biotechnol (1988) vol. 29, No. 2/3, pp. 258 to 263.

K. Ikeda et al., "Synthesis of sialic acid-containing nucleotide sugars: CMP-sialic acid analogs", Carbohydrate Research (1992) vol. 224, No. 7, pp. 123 to 131.

E. Simon et al., "Synthesis of CMP-NeuAc from N-Acetylglucosamine: Generation of CTP from CMP Using Adenylate Kinase", J. Am. Chem. Soc., vol. 110, pp. 7159 to 7163 (1988).

Proceedings of 2001 Annual Conference of the Society for Biotechnology (2001), Japan, with English Translation.

K. Ishige et al., "Novel Method for Enzymatic Synthesis of CMP-NeuAc.," Biosci. Biotechnol. Biochem., Aug. 2001, vol. 65, No. 8, pp. 1736 to 1740.

M. Kittelman, et al., "CMP-N-acetyl neuraminic-acid synthetase from *Escherichia coli*: fermentative production and application for the preparative synthesis of CMP-neuraminic acid", Appl. Microbiol. Biotechnol., Dec. 1995, vol. 44, pp. 59 to 67.

\* cited by examiner

PROCESS FOR PRODUCING CMP-N-ACETYLNEURAMINIC ACID

This application is a U.S. national stage of International Application No. PCT/JP2003/000258 filed Jan. 15, 2003.

TECHNICAL FIELD

The present invention relates to an improved process for producing CMP-N-acetylneuraminic acid (CMP-NeuAc), which is an important material for synthesizing sugar chains.

BACKGROUND ART

In recent years, with the rapid progress of research concerning the structures and functions of sugar chains, research efforts have been undertaken to develop applications of oligosaccharides, glycolipids, glycoproteins, and similar materials having physiological activities in the fields of drugs and functional materials. Among sugar chains, a sialic-acid-containing sugar chain having N-acetylneuraminic acid (NeuAc) at an end thereof plays an important role as a receptor in, for example, cell adhesion or viral infection.

Generally, the sialic-acid-containing sugar chain is synthesized by use of sialyltransferase as a catalyst. Sialyltransferase is an enzyme which catalyzes the transfer of sialic acid from CMP-N-acetylneuraminic acid (CMP-NeuAc), which serves as a sugar donor, to an acceptor such as a sugar chain.

However, CMP-NeuAc employed as a sugar donor is very expensive and therefore has been provided only in small amounts on reagent levels.

In a known method for producing CMP-NeuAc, CMP-NeuAc is synthesized from cytidine 5'-triphosphate (CTP) and NeuAc serving as substrates by use of CMP-NeuAc synthase as a catalyst (Appl. Microbiol. Biotechnol., 44, 59-67(1995)). Since CTP and NeuAc are expensive substances, direct use of these substances as starting materials inevitably increases the cost for producing CMP-NeuAc.

Recently, Koizumi et al. have developed a process for producing CMP-NeuAc from orotic acid and NeuAc as starting materials by using, in combination, *Brevibacterium ammoniagenes* cells which transform orotic acid to uridine 5'-triphosphate (UTP), a recombinant *E. coli* which produces a CTP synthase that catalyzes transformation of UTP to CTP, and a recombinant *E. coli* which produces a CMP-NeuAc synthase (Appl. Microbiol. Biotechnol., 53, 257-261, (2000)). This process does not employ expensive CTP. However, cumbersome steps and large-scale facilities must be provided for preparing cells of a plurality of species, and NeuAc, which is an expensive reagent, is still employed, discouraging employment of the process in practice.

Meanwhile, regarding the method for producing NeuAc, there has been known a process where colominic acid—a polymer of sialic acid—is recovered from a microorganism, and NeuAc is obtained through chemical decomposition of colominic acid. Recently, some processes employing an enzyme have also been developed.

Examples of such enzymatic processes include (1) a process for producing NeuAc from N-acetylmannosamine (ManNAc) by use of NeuAc lyase or NeuAc synthase (J. Am. Chem. Soc., 110, 6481 (1988), J. Am. Chem. Soc., 110, 7159 (1988), and Japanese Patent Application Laid-Open (kokai) No. 10-4961);

(2) a process for producing NeuAc through transformation of N-acetylglucosamine (GlcNAc) to N-acetylmannosamine (ManNAc) under alkaline conditions and subsequent treatment of ManNAc with NeuAc lyase or NeuAc synthase (Japanese Patent Application Laid-Open (kokai) No. 5-211884, Biotechnology And Bioengineering, Vol. 66, No. 2 (1999), and Enzyme Microb. Technol., Vol. 20 (1997)); and (3) a process for producing NeuAc from GlcNAc by use of N-acetylglucosamine (GlcNAc) 2-epimerase which catalyzes transformation of GlcNAc to ManNAc, and NeuAc lyase or NeuAc synthase (WO95/26399, Japanese Patent Application Laid-Open (kokai) Nos. 3-180190, and 2001-136982).

However, these processes have drawbacks. The process (1) employs ManNAc, which is an expensive starting material. Process (2) includes a cumbersome step for isolating ManNAc from a mixture of GlcNAc and ManNAc, although the process employs inexpensive GlcNAc as a starting material. The problem with process (3) resides in that, as shown in the following scheme, it employs GlcNAc 2-epimerase, which functions only in the presence of ATP. Thus, expensive ATP must be used, or ATP must be produced from adenine—a precursor of ATP—by use of a microorganism, making the process unsatisfactory.

<Process (3)>

ATP (or its precursor)

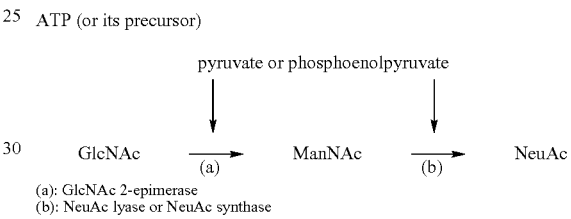

(a): GlcNAc 2-epimerase
(b): NeuAc lyase or NeuAc synthase

DISCLOSURE OF THE INVENTION

The present inventors have studied the synthesis of NeuAc employing GlcNAc as a substrate in the presence of an intracellular enzyme found in *E. coli*, and have found that GlcNAc is transformed to GlcNAc 6-phosphate (GlcNAc-6P) although virtually no NeuAc is synthesized. Thus, the inventors have attempted to establish a NeuAc synthesis system via the following pathway starting with GlcNAc.

As a result, the present inventors have found that NeuAc can be produced at high yield through enhancement of GlcNAc-6P 2-epimerase (EC 5.1.3.9) activity and NeuAc lyase activity or NeuAc synthase activity, and that the synthesis system does not require ATP, which is an expensive reagent.

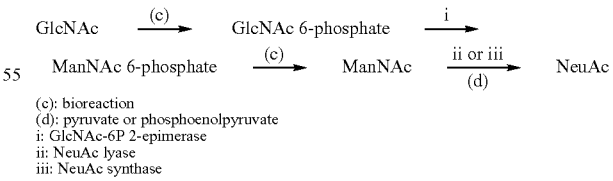

(c): bioreaction
(d): pyruvate or phosphoenolpyruvate
i: GlcNAc-6P 2-epimerase
ii: NeuAc lyase
iii: NeuAc synthase The inventors have further conducted research on a CTP synthesis system including reactions for synthesizing CMP-NeuAc, in an attempt to combine, with the aforementioned NeuAc synthesis system, a microorganism-based transformation system which forms CTP by use of inexpensive CMP as a starting material, and a variety of microorganisms have been tested. The inventors have found that, when a microorganism (e.g., *E. coli*) other than yeast is employed CMP-NeuAc is synthesized only in a small amount, whereas when yeast cells are employed, CMP-NeuAc can be synthesized at high yield. The inventors have also found that phosphoenolpyruvate (PEP) required for NeuAc synthase reaction can be advantageously provided by yeast cells, eliminating the need for further addition of PEP to the reaction system. The present invention has been accomplished on the basis of these findings.

Accordingly, the present invention is directed to a process for producing CMP-N-acetylneuraminic acid (CMP-NeuAc), which comprises adding yeast cells, N-acetylglucosamine-6-phosphate 2-epimerase (GlcNAc-6P 2-epimerase), N-acetylneuraminic acid lyase (NeuAc lyase), and CMP-N-acetylneuraminic acid synthase (CMP-NeuAc synthase) to a reaction system containing N-acetylglucosamine (GlcNAc), pyruvate, and cytidine 5'-monophosphate (CMP) and inducing reaction of the mixture.

The present invention is also directed to a process for producing CMP-N-acetylneuraminic acid (CMP-NeuAc), which comprises adding yeast cells, N-acetylglucosamine-6-phosphate 2-epimerase (GlcNAc-6P 2-epimerase), N-acetylneuraminic acid synthase (NeuAc synthase), and CMP-N-acetylneuraminic acid synthase (CMP-NeuAc synthase) to a reaction system containing N-acetylglucosamine (GlcNAc) and cytidine 5'-monophosphate (CMP) and inducing reaction of the mixture.

BEST MODES FOR CARRYING OUT THE INVENTION

The CMP-NeuAc synthesis routes of the present invention, including a process (A) employing NeuAc lyase and a process (B) employing NeuAc synthase, will next be described with reference to the following schemes. Notably, phosphoenolpyruvate (PEP), which is essential to the reaction system (B), is not required to be added to the system, because PEP is synthesized from glucose contained in culture medium through (metabolic) bioreaction of yeast and *E. coli* and fed to the system.

(A) Process Employing NeuAc Lyase

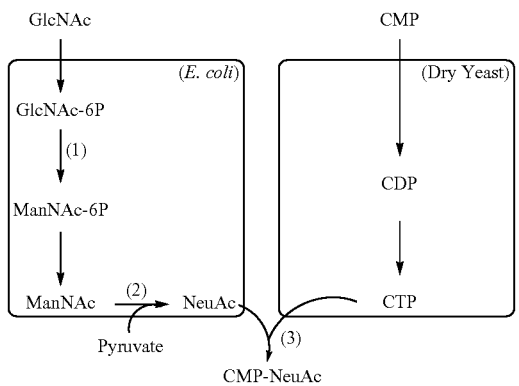

(B) Process Employing NeuAc Synthase

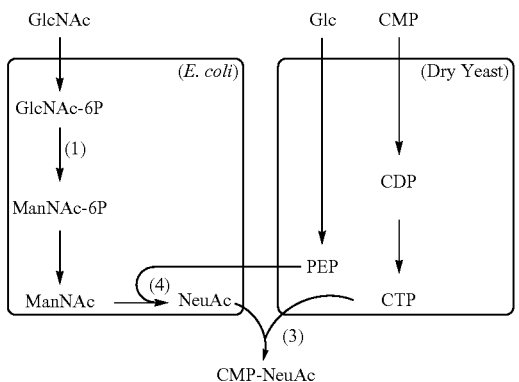

In the above schemes (A) and (B), the reference numerals denote the following:
(1): GlcNAc-6P 2-epimerase
(2): NeuAc lyase
(3): CMP-NeuAc synthase
(4): NeuAc synthase
(1) Preparation of Enzymes and Other Materials N-acetylglucosamine-6-phosphate 2-epimerase (GlcNAc-6P 2-epimerase) ((1) above) which is added to the above reaction system (A) or (B) refers to an enzyme exhibiting catalytic activity on transformation of GlcNAc 6-phosphate to ManNAc 6-phosphate. N-acetylneuraminic acid lyase (NeuAc lyase) ((2) above) which is added to the above reaction system (A) refers to an enzyme exhibiting catalytic activity on reaction of ManNAc and pyruvate serving as substrates, to thereby synthesize NeuAc. N-acetylneuraminic acid synthase (NeuAc synthase) ((4) above) which is added to the above reaction system (B) refers to an enzyme exhibiting catalytic activity on reaction of MaNAc and phosphoenolpyruvate (PEP) serving as substrates, to thereby synthesize NeuAc. CMP-N-acetylneuraminic acid synthase (CMP-NeuAc synthase) ((3) above) which is added to the above reaction system (A) or (B) refers to an enzyme exhibiting a catalytic activity on reaction of NeuAc and CTP serving as substrates, to thereby synthesize CMP-NeuAc.

Examples of enzymes exhibiting such an enzymatic activity include cells (including transformants) and processed products thereof. Among them, enzymes derived from a microorganism are preferably employed, from the viewpoint of ease of preparation and other factors. GlcNAc-6P 2-epimerase, N-acetylneuraminic acid lyase, N-acetylneuraminic acid synthase, and CMP-NeuAc synthase which are derived from a microorganism are known enzymes, and can be prepared through a routine method.

In order to enhance the aforementioned enzyme activity, a so-called recombinant DNA technique is preferably employed. In a specific procedure, genes encoding enzymes are cloned (J. Bacteriol., 181, 47-54, 1999; J. Bacteriol., 181, 4526-4532, 1999; Nucleic Acids. Res., 13, 8843-8852, 1985; Agric. Biol. Chem., 50, 2155-2158, 1986; FEMS Microbiol. Lett., 75, 161-166, 1992; J. Biol. Chem., 271, 15373-15380, 1996; J. Biol. Chem., 264, 14769-14774, 1989; J. Bacteriol., 177, 312-319, 1995; and Mol. Microbiol., 35, 1120-1134, 2000), and the cloned genes are expressed in a large amount of cells of a microorganism.

In the present invention, cells produced through co-expression of two or more genes or a processed product thereof may also be employed. Although no particular limitation is imposed on the above cells, preferred examples include transformants which exhibit enhanced enzyme activity of both GlcNAc-6P 2-epimerase and N-acetylneuraminic acid lyase, and transformants which exhibit enhanced enzyme activity of both GlcNAc-6P 2-epimerase and N-acetylneuraminic acid synthase.

Cloning of genes, preparation of expression vectors by use of a cloned DNA fragment, preparation of enzyme proteins exhibiting an enzyme activity of interest by use of the expression vectors, etc. are techniques known to those skilled in the field of molecular biology, and may be performed through a method described in, for example, "Molecular Cloning" (compiled by Maniatis et al., Cold Spring Harbor Laboratories, Cold Spring Harbor, N.Y. (1982)).

In a specific procedure, probes are synthesized on the basis of a reported nucleotide sequence, and DNA fragments containing a gene encoding an enzyme protein exhibiting an enzyme activity of interest are cloned from chromosomal DNAs of a microorganism. Although no particular limitation is imposed on a host to be employed for cloning, E. coli is preferably employed, from the viewpoint of ease of handling and availability.

In order to establish a high expression system of a cloned gene, the following procedure may be employed. For example, the nucleotide sequence of a cloned DNA fragment is analyzed through the Maxam-Gilbert method (Methods in Enzymology, 65, 499 (1980)), the dideoxy chain termination method (Methods in Enzymology, 101, 20 (1983)), or a similar method, whereby a coding domain of the gene is specified. In order to enable the gene to be expressed in cells of a corresponding host microorganism, a recombinant expression vector containing an expression-regulating signal (transcription initiating signal and translation initiating signal) ligated to the upstream side of the gene is prepared.

A variety of plasmid vectors and phage vectors may be employed. Among them, a plasmid vector which can be replicated in E. coli cells, has an appropriate drug resistant marker and a specific restriction enzyme cleavage site, and permits a large multiplication number within the cells is preferably employed. Specific examples of the plasmid vector include pBR322 (Gene, 2, 95 (1975)), pUC18, and pUC19 (Gene, 33, 103 (1985)).

By use of the thus-prepared recombinant vector, E. coli is transformed. Examples of the E. coli employed as a host include K12 strain, C600, JM105, and JM109 (Gene, 33, 103-119 (1985)), which are employed in recombinant DNA experiments. Alternatively, there may also be employed, as a host, E. coli to which lip gene mutation relating to metabolism of pyruvate has been introduced (e.g., W1485lip2 (ATCC25645)) so as to reduce metabolism of pyruvate other than that which occurs in relation to NeuAc synthesis.

A variety of methods for transforming E. coli have already been reported, and, for example, a plasmid is incorporated into cells through treatment of the cells with calcium chloride at low temperature (J. Mol. Biol., 53, 159 (1970)).

The thus-prepared transformants are cultured in a medium where the corresponding microorganism can grow, and expression of the cloned gene of enzyme protein exhibiting enzyme activity of interest is induced. Culturing is performed until the enzyme protein is accumulated in a large amount within the cells. The transformants may be cultured through a routine method in a medium containing nutrients (e.g., a carbon source and a nitrogen source) required for the growth of the microorganism. In an exemplary procedure, the transformants are cultured in a medium which is generally employed for culturing E. coli (e.g., a bouillon medium, an LB medium (1% trypton, 0.5% yeast extract, and 1% saline), or a 2×YT medium (1.6% trypton, 1% yeast extract, and 0.5% saline)) at 30 to 50° C. for about 10 to 50 hours with, if necessary, aeration and stirring. When a plasmid is employed as a vector, an appropriate antibiotic (in accordance with a drug resistant marker of the plasmid; e.g., ampicillin or kanamycin) is added to the culture in an appropriate amount in order to prevent loss of the plasmid during culturing.

Examples of a mass of cells exhibiting enzyme activity of interest include those collected, from the culture liquid obtained through the above method, through a solid-liquid separation means such as centrifugal separation or membrane separation. Alternatively, there may also be employed, as a cell processed product, a product obtained from processing the thus-collected cell product through a generally employed treatment method such as mechanical breaking (by use of a Waring blender, a French press, a homogenizer, a mortar, etc.), freezing and thawing, autolysis, drying (lyophilization, drying in air, etc.), an enzyme treatment (with lysozyme), ultrasonication, a chemical treatment (with acid, alkali, etc.); or crude or purified enzymes obtained by separating a fraction exhibiting enzyme activity of interest from the cell processed product and subjecting the fraction to a routine enzyme purification means (e.g., salting out, isoelectric precipitation, organic solvent precipitation, dialysis, or chromatographic treatments).

Examples of the yeast employed for transforming CMP to CTP include commercially available bakers' yeasts and wine yeasts. These commercial yeasts are very advantageous, in that a step of producing yeast cells can be omitted. Although either fresh yeast cells or dried yeast cells may be employed, dried yeast cells are preferably employed, from the viewpoint of yield and ease of handling.

(2) Synthesis of CMP-NeuAc

Commercially available products of GlcNAc, pyruvate, and CMP may be employed in CMP-NeuAc synthesis reaction. The concentration of each reagent may be appropriately selected from a range of 1 to 5,000 mM, preferably 10 to 1,000 mM.

(Process Employing NeuAc Lyase)

The CMP-NeuAc synthesis reaction may be carried out by adding GlcNAc-6P 2-epimerase, NeuAc lyase, and CMP-NeuAc synthase, each in an amount of 0.2 mg or more based on 1 mL of reaction solution, preferably 2 to 100 mg, and dry yeast in an amount of 1 to 20% (w/v) to a reaction system containing GlcNAc, CMP, and pyruvate, followed by allowing the mixture to react at 50° C. or lower, preferably 15 to 40° C., for about 1 to 150 hours with, if necessary, stirring.

Alternatively, the above reaction may be performed in two steps so as to improve synthesis yield of CMP-NeuAc. Firstly, GlcNAc-6P 2-epimerase and NeuAc lyase are added to a reaction system containing GlcNAc and pyruvate, and the mixture is allowed to react at 50° C. or lower (preferably 15 to 40° C.) for about 1 to 50 hours, thereby synthesizing NeuAc. Subsequently, CMP, yeast cells, and CMP-NeuAc synthase are added to the reaction mixture, and the mixture is allowed to react for about 5 to 50 hours, thereby synthesizing CMP-NeuAc. Here, in the NeuAc synthesis, CMP may be added in advance to a reaction system.

(Process Employing NeuAc Synthase)

The CMP-NeuAc synthesis reaction may be carried out by adding GlcNAc-6P 2-epimerase, NeuAc synthase, and CMP-NeuAc synthase, each in an amount of 0.2 mg or more based on 1 mL of reaction solution, preferably 2 to 100 mg, and dry yeast in an amount of 1 to 20% (w/v) to a reaction system containing GlcNAc and CMP, followed by allowing the mixture to react at 50° C. or lower (preferably 15 to 40° C.) for about 1 to 150 hours with, if necessary, stirring.

To the aforementioned CMP-NeuAc synthesis systems, an inorganic phosphoric acid, magnesium, and an energy source are preferably added in accordance with needs.

An inorganic phosphoric acid such as potassium phosphate may be used without any modification. However, an inorganic phosphoric acid in the form of a phosphate buffer is preferably used. The concentration of inorganic phosphoric acid may be appropriately selected from a range of 1 to 1,000 mM, preferably 10 to 400 mM. When a phosphate buffer is used, the pH thereof may be appropriately selected from a range of 5 to 10.

Examples of usable magnesium species include inorganic acid magnesium salts such as magnesium sulfate, magnesium nitrate, and magnesium chloride; and organic acid magnesium salts such as magnesium citrate. The concentration of magnesium species may be appropriately selected from a range of 1 to 1,000 mM.

Examples of usable energy sources include sugars such as glucose, fructose, and sucrose; and organic acids such as acetic acid and citric acid. The concentration of energy source may be appropriately selected from a range of 1 to 5,000 mM, preferably 10 to 1,000 mM.

The thus-produced CMP-NeuAc may be isolated and purified through a conventional sugar nucleotide isolation/purification means (e.g., ion exchange chromatography, adsorption chromatography, salting out, or affinity chromatography).

EXAMPLES

Hereinafter, the present invention will be described in more detail by way of Examples, which should not be construed as limiting the invention thereto. In the Examples, preparation of DNA samples, cleavage with restriction enzymes, DNA ligation by use of a T4 DNA ligase, and transformation of $E.$ $coli$ were all performed as described in "Molecular Cloning, A Laboratory Manual, Second Edition" (complied by Sambrook, et al., Cold Spring Harbor Laboratory, Cold Spring Harbor, N.Y. (1989)). Also, restriction enzymes, AmpliTaq DNA polymerase, and T4 DNA ligase were purchased from Takara Bio Inc.

Quantitation of CMP-NeuAc in a reaction mixture was carried out by means of HPLC. Specifically, an ODS-HS302 column (product of YMC) was used for separation, and 1 mM tetrabutylammonium sulfate and 50 mM magnesium acetate solution were used to prepare an eluant. Quantitation of sugar such as NeuAc was carried out by means of HPLC making use of HPAE-PAD. Specifically, a CarboPac PA1 column ED40 (product of Dionex) was used for separation and detection purposes, and solution A (0.1N NaOH) and solution B (0.1N NaOH, 0.5M sodium acetate), with a gradient therebetween, were used to prepare an eluant.

Example 1

(1) Cloning of nanA Gene encoding N-acetylneuraminic Acid Lyase

Chromosomal DNA (ATCC 51907D) of $Haemophilus$ $influenzae$ ($H.$ $influenzae$) Rd strain was used as a template, and the two below-described primer DNA sequences were synthesized according to a method known per se. The N-acetylneuraminic acid lyase (nanA) gene of $H.$ $influenzae$ was amplified through PCR.

```
Primer (A):
                                        (SEQ ID NO: 1)
5'- CACCATGGCGAAGATATTGCCGCTCAAACTA -3'

Primer (B):
                                        (SEQ ID NO: 2)
5'- CCGAATTCATTTATGACAAAAATTTCGCTTTCAAG -3'
```

Amplification of the nanA gene through PCR was performed in a DNA Thermal Cycler (product of Perkin-Elmer Cetus Instrument) by adding thereto a 100 µL reaction mixture containing 50 mM potassium chloride, 10 mM Tris HCl (pH 8.3), 1.5 mM magnesium chloride, 0.001% gelatin, 0.1 µg template DNA, DNA primers (A) and (B) (each 0.2 µM), and AmpliTaq DNA polymerase (2.5 units). The cycling protocol consisted of 25 cycles of the following three steps: strand denaturation at 94° C. for 1 minute, annealing at 55° C. for 1.5 minutes, and polymerization at 72° C. for 3 minutes.

Subsequent to gene amplification, the reaction mixture was treated with a phenol/chloroform (1:1) mixture. To the water-soluble fraction, ethanol was added in a volume twice that of the fraction, to thereby precipitate DNA. The DNA collected through precipitation was subjected to agarose gel electrophoresis as described in literature (Molecular Cloning, see above), to thereby purify DNA fragments having a size of 1.2 kb. The DNA was cleaved with restriction enzymes NcoI and EcoRI, followed by ligation, by use of T4 DNA ligase, with plasmid pTrc99A (Pharmacia Biotech.) which had likewise been digested with restriction enzymes NcoI and EcoRI. By use of the ligation reaction mixture, $E.$ $coli$ strain JM109 (ATCC53323) was transformed, and from the resultant ampicillin-resistant transformants, plasmid pTrcnanA was isolated. pTrcnanA has a structure in which a DNA fragment containing a structural gene of nanA gene of $H.$ $influenzae$ has been inserted to the NcoI-EcoRI cleavage sites located downstream of the trc promoter of pTrc99A.

(2) Cloning of nanE Gene encoding GlcNAc-6P 2-Epimerase

Chromosomal DNA of $H.$ $influenzae$ Rd strain was used as a template, and the two below-described primer DNA sequences were synthesized according to a method known per se. The GlcNAc-6P 2-epimerase (nanE) gene of $H.$ $influenzae$ was amplified through PCR.

```
Primer (C):
                                        (SEQ ID NO: 3)
5'- GGTCTAGATTTAAATGAGGGGTGTTATATGT -3'

Primer (D):
                                        (SEQ ID NO: 4)
5'- TCGTCGACTTATCTTGCAGATTTCACTGAATTAGCAAACCA -3'
```

Amplification of the nanE gene through PCR was performed in a DNA Thermal Cycler (product of Perkin-Elmer Cetus Instrument) by adding thereto a 100 µL reaction mixture containing 50 mM potassium chloride, 10 mM Tris HCl (pH 8.3), 1.5 mM magnesium chloride, 0.001% gelatin, 0.1 µg template DNA, DNA primers (C) and (D) (each 0.2 µM), and AmpliTaq DNA polymerase (2.5 units). The cycling protocol consisted of 25 cycles of the following three steps: strand denaturation at 94° C. for 1 minute, annealing at 55° C. for 1.5 minutes, and polymerization at 72° C. for 3 minutes.

Subsequent to gene amplification, the reaction mixture was treated with a phenol/chloroform (1:1) mixture. To the water-soluble fraction, ethanol was added in a volume twice that of the fraction, to thereby precipitate DNA. The DNA collected through precipitation was subjected to agarose gel electrophoresis as described in literature (Molecular Cloning, see above), to thereby purify DNA fragments having a size of 720 b. The DNA was cleaved with restriction enzymes XbaI and SalI, followed by ligation, by use of T4 DNA ligase, with plasmid pTrc99A which had likewise been digested with restriction enzymes XbaI and SalI. By use of the ligation reaction mixture, E. coli strain JM109 was transformed, and from the resultant ampicillin-resistant transformants, plasmid pTrc-nanE was isolated. pTrc-nanE has a structure in which a DNA fragment containing a structural gene of nanE gene of H. influenzae has been inserted to the XbaI-SalI cleavage sites located downstream of the trc promoter of pTrc99A.

(3) Construction of a Plasmid for Coexpression of nanA and nanE Genes

The pTrcnanA plasmid obtained in above (1) was cleaved with restriction enzymes NcoI and EcoRI, and NcoI-EcoRI fragments containing nanA gene were recovered through agarose gel electrophoresis. The recovered fragments were ligated to the pTrc-nanE plasmid obtained in (2) above through digestion with NcoI and EcoRI, using a T4 DNA ligase. By use of the ligation reaction mixture, E. coli strain JM109 was transformed, and from the resultant ampicillin-resistant transformants, plasmid pTrcAE was isolated. pTrcAE has a structure in which a DNA fragment containing structural genes of nanE and nanA of H. influenzae has been inserted to the NcoI-SalI cleavage sites located downstream of the trc promoter of pTrc99A.

(4) Synthesis of NeuAc

E. coli W1485lip2 (ATCC25645) was engineered so as to harbor the plasmid pTrcAE constructed in (3) above, and inoculated in a 2×YT medium (500 mL) supplemented with 100 μg/mL ampicillin. Shaking culture was performed at 37° C. When the cell count had reached $1 \times 10^8$ cells/mL, isopropyl β-D-thiogalactoside (IPTG) was added to the culture system so as to attain a final concentration of 0.2 mM. Shaking culture was continued at 37° C. for 26 hours. After completion of culturing, the culture was subjected to centrifugal separation (9,000×g, 10 minutes), whereby a 25-mL culture broth (which equals to 50 mg cells) was recovered. To the recovered culture cells was added a potassium phosphate buffer (200 mM, pH 8.0, 5 mL) containing 100 mM GlcNAc, 20 mM magnesium chloride, 50 mM glucose, 300 mM sodium pyruvate, and 0.5% (v/v) xylene, and the mixture was allowed to react at 28° C. under stirring. At points in time 14 and 24 hours after the start of reaction, sodium pyruvate (110 mg) was added, and at 48 hours, the reaction mixture was heat-treated at 100° C. for 5 minutes, whereby reaction was stopped. Analysis of the resultant reaction mixture by means of HPLC (HPAE-PAD, Dionex) designed for sugar analysis confirmed production of 43.7 mM NeuAc.

A control microorganism (E. coli W1485lip2 harboring plasmid pTrc99A) was subjected to similar reactions. However, production of NeuAc was not detected (which means production was 0.5 mM or less).

(5) Cloning of neuA Gene Encoding CMP-NeuAc Synthase

Chromosomal DNA of H. influenzae Rd strain was used as a template, and the two below-described primer DNA sequences were synthesized according to a method known per se. The CMP-NeuAc synthase (neuA) gene of H. influenzae was amplified through PCR.

Primer (E):
(SEQ ID NO: 5)
5'- TGCCATGGTGAAAATAATAATGACAAGAA -3'

Primer (F):
(SEQ ID NO: 6)
5'- AACTGCAGTGCAGATCAAAAGTGCGGCC -3'

Amplification of the neuA gene through PCR was performed in a DNA Thermal Cycler (product of Perkin-Elmer Cetus Instrument) by adding thereto a 100 μL reaction mixture containing 50 mM potassium chloride, 10 mM Tris HCl (pH 8.3), 1.5 mM magnesium chloride, 0.001% gelatin, 0.1 μg template DNA, DNA primers (E) and (F) (each 0.2 μM), and AmpliTaq DNA polymerase (2.5 units). The cycling protocol consisted of 25 cycles of the following three steps: strand denaturation at 94° C. for 1 minute, annealing at 55° C. for 1.5 minutes, and polymerization at 72° C. for 3 minutes.

Subsequent to gene amplification, the reaction mixture was treated with a phenol/chloroform (1:1) mixture. To the water-soluble fraction, ethanol was added in a volume twice that of the fraction, to thereby precipitate DNA. The DNA collected through precipitation was subjected to agarose gel electrophoresis as described in literature (Molecular Cloning, see above), to thereby purify DNA fragments having a size of 720 b. The DNA was cleaved with restriction enzymes NcoI and PstI, followed by ligation, by use of T4 DNA ligase, with plasmid pTrc99A which had likewise been digested with restriction enzymes NcoI and PstI. By use of the ligation reaction mixture, E. coli strain JM109 was transformed, and from the resultant ampicillin-resistant transformants, plasmid pTrcsiaBNP was isolated. pTrcsiaBNP has a structure in which a DNA fragment containing a structural gene of neuA gene of H. influenzae has been inserted to the NcoI-PstI cleavage sites located downstream of the trc promoter of pTrc99A.

(6) Preparation of CMP-NeuAc Synthase

E. coli JM109 harboring the plasmid pTrcsiaBNP was inoculated in a 2×YT medium (100 mL) supplemented with 100 μg/mL ampicillin. Shaking culture was performed at 37° C. When the cell count had reached $4 \times 10^8$ cells/mL, IPTG was added to the culture system so as to attain a final concentration of 0.25 mM. Shaking culture was continued at 37° C. for 6 hours. After completion of culturing, the culture was subjected to centrifugal separation (9,000×g, 10 minutes), whereby the cells were recovered. The cells were suspended in a buffer (5 mL) (100 mM Tris-HCl (pH 7.8), 10 mM $MgCl_2$). The cells were ultrasonically disrupted, and the resultant cell residues were removed through centrifugation (20,000×g, 10 minutes).

The thus-obtained supernatant fraction was employed as an enzyme solution, and CMP-NeuAc synthase activity as measured with this enzyme solution is shown in Table 1 together with the data from a control microorganism (E. coli K-12 JM109 harboring pTrc99A). In the present invention, CMP-NeuAc synthase activity units were determined by measuring and calculating activity in relation to the synthesis of CMP-NeuAc from 5'-CMP and N-acetylneuraminic acid through the below-described method.

(Measurement of CMP-NeuAc Synthase Activity and Calculation of Units)

The CMP-NeuAc synthase was added to 50 mM Tris-HCl buffer (pH 8.0) containing 20 mM magnesium chloride, 5 mM CTP, and 10 mM N-acetylneuraminic acid, to thereby initiate reaction for five minutes at 37° C. As a control, a cell lysate of E. coli JM109 harboring pTrc99A was employed instead of CMP-NeuAc synthase and similar reaction was performed.

To the reaction mixture, 70% ethanol (twice the volume of the mixture) was added to thereby stop the reaction, and the mixture was diluted and then analyzed through HPLC. The separation process was performed through use of an HS-302 column (product of YMC) and, as an eluent, a mixture of 50 mM magnesium acetate and an aqueous 1 mM tetrabutylammonium solution. From the results of the HPLC analysis, amount of CMP-NeuAc contained in the reaction mixture was calculated. The activity of the synthase capable of synthesizing 1 μmole CMP-NeuAc in one minute at 37° C. was regarded as one unit, and the CMP-NeuAc synthase activity was calculated.

TABLE 1

| Microorganism/Plasmid | CMP-NeuAc synthase Activity (units/mg protein) |
|---|---|
| JM109/pTrc99A | <0.01 |
| JM109/pTrcsiaBNP | 2.45 |

(7) Synthesis of CMP-NeuAc

E. coli K-12 ME8417 (FERM BP-6847: Aug. 18, 1999, National Institute of Advanced Industrial Science and Technology, Patent Microorganisms Depositary (Chuo 6, 1-1-1 Higashi, Tsukuba-shi, Ibaraki-ken, Japan (postal code: 305-8566)) was engineered so as to harbor the plasmid pTrcAE constructed in (3) above, and inoculated in a 2×YT medium (500 mL) supplemented with 100 μg/mL ampicillin. Shaking culture was performed at 37° C. When the cell count had reached 4×10$^8$ cells/mL, IPTG was added to the culture system so as to attain a final concentration of 0.2 mM. Shaking culture was continued at 37° C. for 8.5 hours. After completion of culturing, the culture was subjected to centrifugal separation (9,000×g, 10 minutes), whereby a 25-mL culture broth (which equals to 50 mg of cells) were recovered. To the recovered culture cells was added a potassium phosphate buffer (200 mM, pH 8.0, 5 mL) containing 50 mM CMP, 100 mM GlcNAc, 20 mM magnesium chloride, 50 mM glucose, and 250 mM sodium pyruvate, and 0.5% (v/v) xylene, and the mixture was allowed to react at 28° C. under stirring.

Twenty-four hours after the reaction started, dry baker's yeast (product of Oriental Yeast) (250 mg), CMP-NeuAc synthase (3.4 units/mL reaction mixture) prepared in (6) above, and 1M magnesium chloride solution (100 μL) were added to the reaction mixture, and reaction was allowed to proceed for a total of 62 hours. At a point in time 14 hours after the start of reaction, sodium pyruvate (110 mg) was added, at 24 and 38 hours, sodium pyruvate (110 mg) and glucose (180 mg) was added, and, at 48 hours, sodium pyruvate (55 mg) and glucose (180 mg) was added to the reaction mixture.

Analysis of the supernatant of the reaction mixture through HPLC reveals that 21.4 mM CMP-NeuAc was produced.

Comparative Example 1

(1) Cloning of cmk Gene Encoding CMP Kinase

A chromosomal DNA prepared from E. coli JM109 through a method described by Saito and Miura (Biochim. Biopys. Acta., 72, 619 (1963)) was used as a template, and the two below-described primer DNA sequences were synthesized according to a method known per se. The CMP kinase (cmk) gene of E. coli was amplified through PCR.

```
Primer (G):
                                     (SEQ ID NO: 7)
5'- TTGAATTCTAAGGAGATAAAGATGACGGCAATT -3'

Primer (H):
                                     (SEQ ID NO: 8)
5'- TTGAGCTCTGCAAATTCGGTCGCTTATGCG -3'
```

Amplification of the cmk gene through PCR was performed in a DNA Thermal Cycler (product of Perkin-Elmer Cetus Instrument) by adding thereto a 100 μL reaction mixture containing 50 mM potassium chloride, 10 mM Tris HCl (pH 8.3), 1.5 mM magnesium chloride, 0.001% gelatin, 0.1 μg template DNA, DNA primers (G) and (H) (each 0.2 μM), and AmpliTaq DNA polymerase (2.5 units). The cycling protocol consisted of 25 cycles of the following three steps: strand denaturation at 94° C. for 1 minute, annealing at 55° C. for 1.5 minutes, and polymerization at 72° C. for 3 minutes.

Subsequent to gene amplification, the reaction mixture was treated with a phenol/chloroform (1:1) mixture. To the water-soluble fraction, ethanol was added in a volume twice that of the fraction, to thereby precipitate DNA. The DNA collected through precipitation was subjected to agarose gel electrophoresis as described in literature (Molecular Cloning, see above), to thereby purify DNA fragments having a size of 720 b. The DNA was cleaved with restriction enzymes EcoRI and SacI, followed by ligation, by use of T4 DNA ligase, with plasmid pTrc99A which had likewise been digested with restriction enzymes EcoRI and SacI. By use of the ligation reaction mixture, E. coli strain JM109 was transformed, and from the resultant ampicillin-resistant transformants, plasmid pTrcCMKAB was isolated. pTrcCMKAB has a structure in which a DNA fragment containing a structural gene of cmk gene of E. coli has been inserted to the EcoR-SacI cleavage sites located downstream of the trc promoter of pTrc99A.

(2) Construction of a Plasmid for Coexpression of cmk and neuA Genes

The pTrcsiaBNP plasmid obtained in Example 1 was cleaved with restriction enzymes NcoI and EcoRI, and NcoI-EcoRI fragments containing neuA gene were recovered through agarose gel electrophoresis. The recovered fragments were ligated to the pTrcCMKAB plasmid obtained in Comparative Example (1) above through digestion with NcoI and EcoRI, using a T4 ligase. By use of the ligation reaction mixture, E. coli strain JM109 was transformed, and from the resultant ampicillin-resistant transformants, plasmid pTrcSBCK was isolated. pTrcSBCK has a structure in which a DNA fragment containing structural genes of neuA of H. influenzae and cmk of E. Coli has been inserted to the NcoI-SalI cleavage sites located downstream of the trc promoter of pTrc99A.

(3) Synthesis of CMP-NeuAc

A 25-mL culture broth (equivalent to 50-mg cells) of E. coli ME8417/pTrcAE prepared in Example 1 was added to 200 mM potassium phosphate buffer (pH 8.0, 2.5 mL) containing 100 mM GlcNAc, 20 mM magnesium chloride, 50 mM glucose, 250 mM sodium pyruvate, and 0.5% (v/v) xylene. The mixture was allowed to react under stirring for 24 hours at 28° C.

A 25-mL culture broth (equivalent to 50-mg cells) of E. coli ME8417 harboring the plasmid pTrcSBCK constructed in (2) above was added to 200 mM potassium phosphate buffer (pH 8.0, 2.5 mL) containing 100 mM CMP, 20 mM magnesium chloride, and 250 mM sodium pyruvate, followed by ultrasonic treatment.

The ultrasonic-treated solution (2.5 mL) was added to the reaction mixture 24 hours after the reaction started, and the resultant mixture was further allowed to react under stirring at 28° C. At points in time 14 and 24 hours after the start of reaction, 55 mg of sodium pyruvate was added, and, at 38 hours, 110 mg of sodium pyruvate was added thereto.

After reaction was allowed to proceed for a total of 48 hours, the supernatant of the reaction mixture was analyzed through HPLC. The results indicate that 6.28 mM CMP-NeuAc was produced.

Example 2

(1) Cloning of neuB1 Gene Encoding N-Acetylneuraminic Acid Synthase

Chromosomal DNA of *Campylobacter jejuni* 1652 strain was used as a template, and the two below-described primer DNA sequences were synthesized according to a method known per se. The acetylneuraminic acid synthase (neuB1) gene was amplified through PCR.

```
                                              (SEQ ID NO: 9)
Primer (I):   5'- TACGATTATTTTCCTGATGCTC -3'

(SEQ ID NO: 10)
Primer (J):   5'- TCTCCAAGCTGCATTAAACGCC -3'
```

Amplification of the neuB1 gene through PCR was performed in a DNA Thermal Cycler (product of Perkin-Elmer Cetus Instrument) by adding thereto a 100 µL reaction mixture containing 50 mM potassium chloride, 10 mM Tris HCl (pH 8.3), 1.5 mM magnesium chloride, 0.001% gelatin, 0.1 µg template DNA, DNA primers (I) and (J) (each 0.2 µM), and AmpliTaq DNA polymerase (2.5 units). The cycling protocol consisted of 30 cycles of the following three steps: strand denaturation at 94° C. for 1 minute, annealing at 55° C. for 1.5 minutes, and polymerization at 72° C. for 3 minutes.

Subsequent to gene amplification, the reaction mixture was treated with a phenol/chloroform (1:1) mixture. To the water-soluble fraction, ethanol was added in a volume twice that of the fraction, to thereby precipitate DNA. The DNA collected through precipitation was subjected to agarose gel electrophoresis as described in literature (Molecular Cloning, see above), to thereby purify DNA fragments having a size of 2.2 kb. The DNA fragments were used as a template, and the two below-described primer DNA sequences were synthesized according to a method known per se. The neuB1 gene of *C. jejuni* was again amplified through PCR.

```
                                              (SEQ ID NO: 11)
Primer (K): 5'-AAGGATCCTCTAGTGAGGCTTATGGAA-3'

(SEQ ID NO: 12)
Primer (L): 5'-GTCTGCAGATTTAATCTTAGAATAATCAGCCC-3'
```

Amplification of the neuB1 gene through PCR was performed in a DNA Thermal Cycler (product of Perkin-Elmer Cetus Instrument) by adding thereto a 100 µL reaction mixture containing 50 mM potassium chloride, 10 mM Tris HCl (pH 8.3), 1.5 mM magnesium chloride, 0.001% gelatin, 0.1 µg template DNA, DNA primers (A) (K) and (L) (each 0.2 µM), and AmpliTaq DNA polymerase (2.5 units). The cycling protocol consisted of 25 cycles of the following three steps: strand denaturation at 94° C. for 1 minute, annealing at 55° C. for 1.5 minutes, and polymerization at 72° C. for 3 minutes.

Subsequent to gene amplification, the reaction mixture was treated with a phenol/chloroform (1:1) mixture. To the water-soluble fraction, ethanol was added in a volume twice that of the fraction, to thereby precipitate DNA. The DNA collected through precipitation was subjected to agarose gel electrophoresis, to thereby purify DNA fragments having a size of 1.2 kb. The DNA was cleaved with restriction enzymes BamHI and PstI, followed by ligation, by use of T4 DNA ligase, with plasmid pTrc99A (Pharmacia Biotech.) which had likewise been digested with restriction enzymes BamHI and PstI. By use of the ligation reaction mixture, *E. coli* strain JM109 was transformed, and from the resultant ampicillin-resistant transformants, plasmid pTrcneuB1 was isolated. pTrcneuB1 has a structure in which a DNA fragment containing a structural gene of neuB1 gene of *C. jejuni* has been inserted to the BamHI-PstI cleavage sites located downstream of the trc promoter of pTrc99A (FERM BP-8248: Jun. 25, 2002, National Institute of Advanced Industrial Science and Technology, Patent Microorganisms Depositary (Chuo 6, 1-1-1 Higashi, Tsukuba-shi, Ibaraki-ken, Japan (postal code: 305-8566)).

(2) Construction of a Plasmid for Coexpression of nanE and neuB1 Genes

The pTrcneuB1 plasmid prepared in (1) above was cleaved with a restriction enzyme BamHI and blunted with a T4 DNA polymerase. The product was cleaved with a restriction enzyme PstI, and (BamHI)-PstI fragments containing neuB1 gene were collected through agarose gel electrophoresis. Subsequently, the pTrcnanE plasmid prepared in Example 1 (2) was cleaved with a restriction enzyme SalI and blunted with a T4 DNA polymerase, and then cleaved with a restriction enzyme PstI. The resultant fragments were ligated to the (BamHI)-PstI fragments containing neuB1 gene using a T4 DNA ligase. By use of the ligation reaction mixture, *E. coli* strain JM109 was transformed, and from the resultant ampicillin-resistant transformants, plasmid pTrcNENB was isolated. pTrcNENB has a structure in which a DNA fragment containing structural genes of nanE of *H. influenzae* and neuB1 of *C. jejuni* has been inserted to the XbaI-PstI cleavage sites located downstream of the trc promoter of pTrc99A.

(3) Synthesis of CMP-NeuAc

*E. coli* MC1061 (ATCC53338) was engineered so as to harbor the plasmid pTrcNENB constructed in (2) above. To the cultured cell (50 mg) were added 175 mM potassium phosphate buffer (pH 8.0) (5 mL) containing 50 mM CMP, 100 mM GlcNAc, 30 mM magnesium chloride, 200 mM glucose, 100 mM sodium pyruvate, 0.5% (v/v) xylene, 4% (w/v) dry baker's yeast (product of Oriental yeast), and CMP-NeuAc synthase (1.7 units/mL reaction mixture) prepared in Example 1 (6). Reaction was allowed to proceed under stirring for 72 hours at 28° C. At points in time 14, 24, 38, 48, and 62 hours after the start of reaction, glucose (180 mg) was added to the mixture.

Analysis of the supernatant of the reaction mixture through HPLC reveals that 25.6 mM CMP-NeuAc was produced.

INDUSTRIAL APPLICABILITY

The process of the present invention employing NeuAc lyase requires no expensive ATP and enables, for the first time, efficient production of CMP-NeuAc from inexpensive GlcNAc, CMP, and pyruvate. Therefore, the process of the present invention is considerably useful as a process for mass-production of CMP-NeuAc.

The process of the present invention employing NeuAc synthase also requires no expensive ATP and enables, for the first time, efficient production of CMP-NeuAc from inexpensive GlcNAc, CMP, and pyruvate, since phosphoenolpyruvate (PEP), which is essential to the NeuAc synthase reaction, is synthesized and supplied from glucose through (metabolic)

bioreaction of yeast and *E. coli*, omitting the need of addition of phosphoenolpyruvate (PEP) to the reaction system. Therefore, the process of the present invention is considerably useful as a process for mass-production of CMP-NeuAc.

In particular, the process of the present invention employing NeuAc synthase is simple and excellent as compared with the process of the present invention employing NeuAc lyase, which requires two steps of reaction.

The invention claimed is:

1. A process for producing CMP-N-acetylneuraminic acid (CMP-NeuAc), comprising:
   i) culturing *Escherichia coli* cells which has been transformed with both the DNA encoding N-acetylglucosamine-6-phosphate 2-epimerase (GlcNAc-6P 2-epimerase) and the DNA encoding N-acetylneuraminic acid synthase (NeuAc synthase) and as the result of being transformed said *Escherichia coli* cells exhibit the activities of N-acetylglucosamine-6-phosphate 2-epimerase (GlcNAc-6P 2-epimerase) and N-acetylneuraminic acid synthase (NeuAc synthase) in a medium,
   ii) adding a phosphate buffer of pH 8.0, containing baker's yeast cells, CMP, N-acetylglucosamine (GlcNAc), magnesium, xylene, glucose, and CMP-N-acetylneuraminic acid synthase (CMP-NeuAc synthase) to said cultured cells to provide a reaction mixture, and
   iii) allowing the reaction to proceed by stirring the mixture for 72 hours at 28° C. and producing CMP-N-acetylneuraminic acid (CMP-NeuAc), wherein the process does not require adding ATP.

* * * * *

SEQUENCE LISTING

```
<160> NUMBER OF SEQ ID NOS: 12

<210> SEQ ID NO 1
<211> LENGTH: 31
<212> TYPE: DNA
<213> ORGANISM: Artificial Sequence
<220> FEATURE:
<223> OTHER INFORMATION: primer for amplification of nanA gene

<400> SEQUENCE: 1
caccatggcg aagatattgc cgctcaaact a                              31

<210> SEQ ID NO 2
<211> LENGTH: 35
<212> TYPE: DNA
<213> ORGANISM: Artificial Sequence
<220> FEATURE:
<223> OTHER INFORMATION: primer for amplification of nanA gene

<400> SEQUENCE: 2
ccgaattcat ttatgacaaa aatttcgctt tcaag                          35

<210> SEQ ID NO 3
<211> LENGTH: 31
<212> TYPE: DNA
<213> ORGANISM: Artificial Sequence
<220> FEATURE:
<223> OTHER INFORMATION: primer for amplification of nanE gene

<400> SEQUENCE: 3
ggtctagatt taaatgaggg gtgttatatg t                              31

<210> SEQ ID NO 4
<211> LENGTH: 41
<212> TYPE: DNA
<213> ORGANISM: Artificial Sequence
<220> FEATURE:
<223> OTHER INFORMATION: primer for amplification of nanE gene

<400> SEQUENCE: 4
tcgtcgactt atcttgcaga tttcactgaa ttagcaaacc a                   41

<210> SEQ ID NO 5
<211> LENGTH: 29
<212> TYPE: DNA
<213> ORGANISM: Artificial Sequence
<220> FEATURE:
<223> OTHER INFORMATION: primer for amplification of neuA gene

<400> SEQUENCE: 5
tgccatggtg aaaataataa tgacaagaa                                 29

<210> SEQ ID NO 6
<211> LENGTH: 28
<212> TYPE: DNA
<213> ORGANISM: Artificial Sequence
<220> FEATURE:
<223> OTHER INFORMATION: primer for amplification of neuA gene

<400> SEQUENCE: 6
```

```
aactgcagtg cagatcaaaa gtgcggcc                                              28
```

<210> SEQ ID NO 7
<211> LENGTH: 33
<212> TYPE: DNA
<213> ORGANISM: Artificial Sequence
<220> FEATURE:
<223> OTHER INFORMATION: primer for amplification of cmk gene

<400> SEQUENCE: 7

```
ttgaattcta aggagataaa gatgacggca att                                        33
```

<210> SEQ ID NO 8
<211> LENGTH: 30
<212> TYPE: DNA
<213> ORGANISM: Artificial Sequence
<220> FEATURE:
<223> OTHER INFORMATION: primer for amplification of cmk gene

<400> SEQUENCE: 8

```
ttgagctctg caaattcggt cgcttatgcg                                            30
```

<210> SEQ ID NO 9
<211> LENGTH: 22
<212> TYPE: DNA
<213> ORGANISM: Artificial Sequence
<220> FEATURE:
<223> OTHER INFORMATION: primer for amplification of neuB1 gene

<400> SEQUENCE: 9

```
tacgattatt ttcctgatgc tc                                                    22
```

<210> SEQ ID NO 10
<211> LENGTH: 22
<212> TYPE: DNA
<213> ORGANISM: Artificial Sequence
<220> FEATURE:
<223> OTHER INFORMATION: primer for amplification of neuB1 gene

<400> SEQUENCE: 10

```
tctccaagct gcattaaacg cc                                                    22
```

<210> SEQ ID NO 11
<211> LENGTH: 27
<212> TYPE: DNA
<213> ORGANISM: Artificial Sequence
<220> FEATURE:
<223> OTHER INFORMATION: primer for amplification of neuB1 gene

<400> SEQUENCE: 11

```
aaggatcctc tagtgaggct tatggaa                                               27
```

<210> SEQ ID NO 12
<211> LENGTH: 32
<212> TYPE: DNA
<213> ORGANISM: Artificial Sequence
<220> FEATURE:
<223> OTHER INFORMATION: primer for amplification of neuB1 gene

<400> SEQUENCE: 12

```
gtctgcagat ttaatcttag aataatcagc cc                                         32
```